US006224876B1

(12) United States Patent
Kesharlal et al.

(10) Patent No.: US 6,224,876 B1
(45) Date of Patent: May 1, 2001

(54) ISOLATION AND FORMULATIONS OF NUTRIENT-RICH CAROTENOIDS

(76) Inventors: Biyani Milind Kesharlal, 11, Shivam, Malbar Hill Road, Mumbai-400 082; Simha Nanda Pratap, Kaustubh Society, Block No. 9, Adarsh, Nagar, Kopri, Thane, (E)-400603; Biyani Sushma Milind, 11, Shivam, Malbar Hill Road, Mumbai-400 082; Nunes Priya Ann, 23A, St. Dominic's Road, Mumbai-400 050; Gupta Sanjay Harnarayan, 4, Radhabai Building, Pandit Solicitor Lane, Rani Sati Marg, Mumbai-400 097, all of (IN)

( * ) Notice: Subject to any disclaimer, the term of this patent is extended or adjusted under 35 U.S.C. 154(b) by 0 days.

(21) Appl. No.: 09/460,118

(22) Filed: Dec. 13, 1999

Related U.S. Application Data

(62) Division of application No. 09/130,350, filed on Aug. 4, 1998, now Pat. No. 6,056,962.

(51) Int. Cl.[7] ................................................... A61K 35/78
(52) U.S. Cl. ......................................................... 424/195.1
(58) Field of Search .............................. 424/195.1; 426/2

(56) References Cited

U.S. PATENT DOCUMENTS

| 2,567,362 | * | 9/1951 | Berkman et al. ................. 424/195.1 |
| 2,739,145 | * | 3/1956 | Barnett ................................. 530/370 |
| 2,848,508 | * | 8/1958 | Barnett et al. ....................... 585/803 |
| 5,245,095 | * | 9/1993 | Graves et al. ....................... 585/351 |
| 5,292,538 | * | 3/1994 | Paul et al. ............................. 426/74 |
| 5,476,678 | * | 12/1995 | Walter et al. ........................ 426/660 |
| 5,549,905 | * | 8/1996 | Mark et al. ........................... 424/439 |
| 5,589,468 | * | 12/1996 | Lin et al. ............................... 514/52 |
| 5,641,531 | * | 6/1997 | Liebrecht et al. .................... 426/583 |
| 5,686,429 | * | 11/1997 | Lin et al. ............................... 514/52 |
| 5,830,738 | * | 11/1998 | Thomas et al. ...................... 435/209 |

* cited by examiner

Primary Examiner—Jean C. Witz
(74) Attorney, Agent, or Firm—Bierman, Muserlian and Lucas

(57) ABSTRACT

Pharmacologically and biologically active compositions containing carotenoids, in combination with micro and macro nutrients, a process for their preparation from carrots and their use in formulations for health care and nutrition applications. The process includes sequentially treating carrot juice with a carboxylic acid and a saccharide to obtain a carotenoid fraction rich in micro and macro nutrients in proportions compatible with those originally found in the natural state. A method of treating retenoid deficient states and immunomodulation is also disclosed using the composition.

8 Claims, No Drawings

ISOLATION AND FORMULATIONS OF NUTRIENT-RICH CAROTENOIDS

This is a Division of Ser. No. 09/130,350 filed Aug. 4, 1998 now U.S. Pat. No. 6,056,962.

FIELD OF THE INVENTION

The invention relates to pharmacologically and biologically active compositions containing carotenoids, micro and macro nutrients, a process for their preparation from carrots and their use in formulations for health care and nutrition applications.

BACKGROUND OF THE INVENTION

Carotenoids are a class of naturally-occuring yellow, orange or red tetraterpenoids, found in traces in plant tissue, algae, bacteria and fungi. In particular they are found in vegetable sources such as carrots, spinach, tomatoes and fruits, such as, mango, peach, pumpkim, pappaya. The more commonly known carotenoids are, alpha-carotene, beta-carotene, lutein, zeaxanthin, lycopene and cryptoxanthin.

Carotenoids possess significant nutritional value, carotenes and cryptoxanthin being considered as a provitamin A precursor for the formation of retinal and Vitamin A in humans. Vitamin A, an essential vitamin, for life is not synthesized in the animal cell.

Because carotenoids occur naturally in only trace amounts, the carotenoids must be extracted in concentrated form in order to be useful. Further carotenoids are sensitive to oxygen, air, heat and light.

Nutritionists advocate the the daily use of carrots apart from other fresh vegetables and fruits in diet. Carrots are grown seasonally and good quality carrots are not available throughout the year at affordable prices. A little advertised fact about carrots is that only 20% of the total carotenes present are absorbed even when carrots are eaten in a finely grated form. The percentage of absorption from coarsely grated raw or cooked carrots is still less being around 5%.

The low absorption is attributed to the poor permeability of the cellulosic cell wall to carotenes even after cooking with the result that the major part remains enclosed within the cells. Hence as a source for deriving Vitamin A and use by themselves, carotenoid supplements free from cellulose are strongly recommended. Another advantage of using provitamin A carotenoids is that indiscriminate use of Vitamin A leads to serious toxic effects (Hypervitaminosis) whereas even in large doses carotenoids are harmless.

U.S. Pat. No. 2,567,362 describes fractional centrifugation process for the separation of colloidal dispersoids of active plant pigment units from the generated vegetable hydrosol.

U.S. Pat. No. 2,739,145 describes the separation of coagulated carotenoid-protein particles following heating of a suspension of the vegetable fibre-separated particles in vegetable serum.

U.K. patent 776,405 describes a carotene-concentrate used as a foodstuff for animals using calcium hydroxide and subsequent pH adjustment with phosphoric acid and then with formic acid.

U.S. Pat. No. 2,848,508 describes a process for recovery of carotene from carrots and provides a saturated solution of carotene in natural carrot oil from carrots.

WTO 86/04059 describes the use of a pectolytic enzyme followed by ultrafiltration for extracting and concentrating carotene.

U.S. Pat. No. 5,245,095 describes the use of calcium chloride, calcium hydroxide, calcium lactate or calcium gluconate to extract carotenoids from natural sources.

None of the above or any known processes provide a composition containing carotenoids in combination with micro and macro nutrients, the carotenoids being bound in moieties as in the natural source of carotenoids.

NATURE OF THE INVENTION

In recent times, carotenoids have been found in epidemiological observations to display protective activity as physiological antioxidants, thus reducing the risks of development of several chronic disorders such as heart diseases, cancer, cataract and other ailments. Holistic systems of medicine have, however, for centuries been advocating the synergistic value of dispensing not just pure but natural product ingredients. Use of pharmacologically or biologically active plant extracts is well-known.

Naturally occurring plant material contain a series of closely-related compounds produced naturally via biological and biochemical reactions. The plant is capable of producing a wide range of analogues at least one of which possesses the desired receptor compatibility. However, the related compounds appear to exercise a synergistic effect on the pharmacological or biological activity of the compatible compound and at the same time suppress toxic effects. Therefore the use of a composite set of nutrients as they are present in the natural source, is rapidly gaining supporters in modern medicine.

However, a major drawback in using plant material in its crude form or to use the plant material in its natural state, is that the dosages required of such material, to be therapeutically beneficial, are quite high. For example for receiving the therapeutic supply of carotenoids about one Kg of good quality carrots will have to be consumed every day. Such quantities cannot be conveniently converted into suitable dosage forms.

This invention, therefore, seeks to disclose a process for obtaining a pharmacologically or biologically active plant extract substantially as it occurs in its natural state suitable for converting in a convenient administrable dosage form. The process according to this invention, seeks to provide a concentrated plant extract, in which the plant extract comprises all pharmacologically or biologically active chemicals in the proportions as they exist in the original natural state without the use of organic solvents at any stage of its manufacture and avoiding the use of oils, enzymes, mineral acids, alkalis, metal salts and treatment by temperature in excess of 60 degrees celsius.

The advantage of naturally occurring series and analogues of compounds is achieved without compromising the overall effects of these compounds.

There is no report to date of a product which is standardised in respect of both the carotenoids content as well as the micro and macro nutrients with which the carotenoids are bound to and associated in its natural state occurring in vegetables, particularly carrots.

The present invention describes for the first time biologically or pharmacologically active material obtained from carrots, standardised with respect to its content of carotenoids, vitamins, proteins, lipids, carbohydrates, mineral and trace elements.

The present invention also describes a process to obtain the said material from carrots, which process comprises the addition of a carboxylic acid as herein defined to appropriately processed carrots, followed by the addition of a carbohydrate as herein defined, separation of a carotenoids-rich paste, and subsequent drying.

The present invention also describes the use of the biologically or pharmacologically active material in the preparation of formulations for health care and nutrition applications for use in as variety of prophylactic and therapeutic conditions.

SUMMARY OF THE INVENTION

According to this invention there is provided a pharmacologically and biologically active composition extracted from carrots, including 0.25–5% mass as a percentage of total mass of extract of active carotenoid fraction, absorbable by an animal or human body in a convenient dosage form, in combination with micro and macro nutrients aiding in the absorption, assimilation and supplementing the action of the carotenoid fraction.

Typically, the carotenoid fraction includes alpha-carotene, beta-carotene, lutein, zeaxanthin and lycopene.

Typically the micro nutrients are 0.01 to 1% vitamins, particularly the B complex vitamin, B1, B2, niacin and Vitamin C and 3 to 10% of minerals and trace elements, as a percentage of total mass of extract.

Typically, the macro nutrients are 20–40% lipids, 10–50% proteins and 1 to 25% carbohydrates as a percentage of total mass of extract.

The invention also provides a process for making a pharmacologically and biologically active composition extracted from carrots comprising the steps of comminuting cleaned and washed carrots to obtain a homogeneous comminution;

separating the juice from the comminution by filtration;

treating the juice with a carboxylic acid to adjust the pH of the juice to between 3 and 6;

treating the pH adjusted juice with at least one saccharide;

centrifuging the saccharide containing juice to obtain the composition in a paste form.

In accordance with another embodiment of this invention the process includes a further step of drying the paste in vacuum and pulverizing the solid material so formed to obtain the composition in particulate form.

Typically, the carboxylic acid is at least one acid selected from a group consisting of mono carboxylic acid such as, ascorbic acid and/or sorbic acid, and/or a dicarboxylic acid such as adipic acid, malic acid, fumaric acid or tartaric acid or mixtures of them, and/or a tricarboxylic acid such as citric acid, in solid form or as a saturated aqueous solution in an amount of acid equivalent to 0.03–3.0% mass of juice.

Typically, the saccharide is at least one selected from a group consisting of monosaccharide such as fructose and/or dextrose, and/or a disaccharide such as sucrose, lactose, and/or hexitols such as mannitol, sorbitol, either in solid form or as a saturated aqueous solution, in an amount of saccharide ranging from 1–50% of the juice, preferably 20–30% of the mass of juice.

According to this invention there is further provided a method of treating the human or animal body, therapeutically or prophylactically for conditions arising from a retenoid deficiency state, oxidative stress, Wald's cycle aberration, pathological keratinzation, malignancies or for immunomodulation, by administering orally in suitable tablet, capsule or liquid dosage form or topically a pharmaceutical or biological composition which contains, extracted from carrots, a 0.25 to 5% mass of active carotenoid fraction as a percentage of total mass of extract in combination with micro and macro nutrients aiding in the absorption, assimilation and supplementing the action of the carotenoid fraction.

In accordance with one preferred embodiment of this invention the method also provides for including in the administered composition therapeutic amounts of at least one substance selected from a group containing spirulina, Vitamin E, Vitamin C, selenium compounds, zinc compounds,naturally occurring carotenoids such as those found in algae, fruits and vegetables.

In the sub therapeutic form the pharmacologically and biologically active composition extracted from carrots can be used as a biocompatible pigment.

DETAILED DESCRIPTION OF THE INVENTION

A principal object of the present invention is to provide a pharmacologically and biologically active composition extracted from carrots (Daucus carota L), including 0.25–5% mass as a percentage of total mass of extract of active carotenoid fraction, absorbable by an animal or human body in a convenient dosage form, in combination with micro and macro nutrients aiding in the absorption, assimilation and supplementing the action of the carotenoid fraction.

A feature of this invention is that the extracted composition is compatible with the different natural constituents of the composition, namely the individual and total carotenoids, vitamins, proteins, lipids, carbohydrates, minerals and trace elements and other such naturally-occurring constituents as analyzed by methods known in the literature. The amount of different naturally occurring constituents of carrots, is determined to lie within the ranges specified in the description below and in the accompanying examples. Generally for carrots, the ranges per 100 grams of isolated powder is 250–5000 mg total carotenoids,is 10–1000 mg vitamins, 10–50 g proteins, 20–40 g lipids, 1–25 g carbohydrates and 3–10 g minerals & trace elements.

A second object of the present invention is to describe a novel process for the preparation of the composition from carrots. As one particular example according to the invention, fresh, hard, good quality, orange or red colored carrots with a smooth surface are selected. Different reddish varieties of carrots such as for example "Pusa Kesar", "Pusa Meghali", "Desi Red" are available. Orange-coloured varieties such as "Bangalore local" and "Ooty Hybrid" are known to be rich in beta-carotene, while the reddish-coloured varieties are more rich in lycopene. The carrots are thus selected for process depending on the nature of the composition to be prepared. Defective carrots are eliminated or excluded in the sorting out process. The selected carrots are washed thoroughly with water and comminuted in an appropriate mill, typically a fruit mill which consists of a rotating stainless steel blades whose speed of rotation is adjustable to between 100 to 1000 rpm and which is fitted with a sieve with apertures variable from 1 to 10 mm to control the particle size of the homogeneous comminution. The comminution is treated through a filter press or a coarse filter (50–150 microns) for the purpose of separating the pulp from the juice. To the juice is added with stirring a mono-carboxylic acid such as ascorbic acid, and/or sorbic acid, and/or a dicarboxylic acid such as adipic acid, malic acid, fumaric acid or tartaric acid or mixtures of them, and/or a tricarboxylic acid such as citric acid, in solid form or as a saturated aqueous solution in an amount of acid equivalent to 0.03–3.0% of the liquid, such that a pH value of the resulting mixture of about 3.0–6.0, preferably 5.0 is reached. This helps to build up the particle size of colloidal carotenoid complexes enabling the further processing of the juice by filtration or centrifuging. The carboxylic acids also stabilise the juice during processing. To the resulting solution or suspension is added one or more components of a monosaccharide such as fructose and/or dextrose, and/or a disaccharide such as sucrose, lactose, and/or hexitols such as mannitol, sorbitol, either in solid form or as a saturated aqueous solution, in an amount of saccharide ranging from 1–50% of the juice, in particular 20–30% of the carrot juice, which mixture is subjected to centrifugation to provide carotenoids-rich carrot paste containing 0.1–1.0% carotenoids. It has been observed that the use of saccharides not only increases the stability of the carotenoid fraction but also is instrumental in extracting the carotenoid fraction bound to lipoproteins in combination with micronutrients such as the B-complex vitamins and minerals. In the absence of the saccharides step, the concentration of micro nutrients in the final composition is less than 50 per cent. Moreover, in the absence of the above, the carotenoids degrade within a few months storage. The carotenoids-rich paste can be used as such or after drying under high vacuum, pulverizing and sieving through appropriately sized sieves by which the pharmacologically and biologically active composition of the invention is obtained in powder form.

The powder is analyzed according to known procedures to provide the precise composition of the carotenoids, vitamins, minerals & trace elements, proteins, carbohydrates and lipids in the powder.

The present invention also describes the use of the paste or powder of the invention in health care and nutrition applications and as a colouring agent. The paste can be formulated as an emulsion or suspension for oral or topical use or as a colouring matter using appropriate excipients and adjuvants known to those skilled in the formulations art. The powder can be formulated as solid dosage forms for oral use as powder/granules or as capsules/tablets. These can also be combined with other antioxidants, minerals, vitamins and other micronutrients. Carotenoids act as lipid phase antioxidants. However beta-carotene supplementation alone does not appear to reduce the susceptibility of LDL to oxidation. The present invention also discloses a method of treating the human or animal body, therapeutically or prophylactically for conditions arising from a retenoid deficiency state, oxidative stress, Wald's cycle aberration, pathological keratinzation, malignancies or for immunomodulation, LDL cholesterol reduction, cancer adjuvant therapy and reducing risk of cardiovascular disease by administering orally in suitable tablet, capsule or liquid dosage form or topically a pharmaceutical or biological composition which contain extracted form carrots, a 0.25 to 5% mass of active carotenoid fraction as a percentage of total mass of extract in combination with micro and macro nutrients aiding in the absorption and assimilation and supplementing the action of the carotenoid fraction. Inflammatory and allergic manifestations in the living cell are thought to be the direct cause of hyperactivity of immune function entities in non-specific immunity, whereas the suppression or deficiency of immune functions are the result of hypoactivity. The functioning and efficiency of non-specific immunity may be influenced by many exogenous and endogeneous factors like physical and psychological, oxidant or hyperoxidative stress, hormonal imbalance, pharmaceuticals and the like. A recent trend in medicine is to consider all disease from the molecular perspective, in which derangements in the structures or conformations of vital biomolecules in diseased states are intricately implicated in the aetiopathogenesis of those diseased conditions.

'Immunomodulation' is any procedure which can alter non specific immunity by interfering with its functioning. If it results in enhancement of immune reactions, it results in immunostimulation and primarily implies stimulation of the non specific immunity, that is stimulation of the function and efficiency of granulocytes, macrophages, natural killer cells, complement and properdin, and the various effector substances including interleukins, tumour necrosis factor, interferons, lysozymes, prostaglandins, oxygen radicals and other mediators. Immunosuppression mainly implies reduced resistance against infections and stress and may be due to environmental or chemotherapeutic factors.

Immunostimulation and immunosuppression both need to be addressed in order to regulate normal immunological functioning. Hence, immunostimulating and immunosuppressing agents both have their own standing. There are a variety of known immunosuppressing agents, for instance cyclosporin, however few immunostimulating agents are available. Apart from specific stimulative or suppressive activity, it is believed that certain agents of plant origin such as the carotenoids have the activity to normalize or modulate pathophysiological processes in the underlying immune response and hence the term immunomodulation or immunomodulatory agents or adaptogenic agents are used for these agents. This activity is believed to be dose dependant as can be seen from the immunostimulation at low dilutions of many immunosuppressants. Thus in a biological system, active material will act as an immunostimulant in low doses but as an immunosuppresant in high doses. Such a biologically active material can be called as an 'immunomodulator'.

Biological membranes contain phospholipids (PLs) and degradation of these by oxygen can cause loss of cell integrity. PLs contain high quantities of polyunsaturated fatty acids (PUFAs) and the double bonds of these fatty acids are easily attacked by oxygen to produce toxic fatty peroxides. The extent of formation of peroxides (peroxidation) increases with the number of double bonds in the fatty acids of the PLs, so membranes with a high PUFA content are specially likely to be more oxidized. A common example of peroxidation is rancidity of butter and vegetable oils. Another agent produced within and without the cell is called a free radical. These substances are highly reactive because they are chemically incomplete and hence unstable, so they can latch on to other substances very readily. They are also known as super oxide radicals (singlet oxygen) and they are produced within the cells both by by self-oxidation (as in peroxides) and by enzymatic processes. Their high intrinsic reactivity and their ability to generate even more potent oxidizing agents when combined with peroxides constitutes a constant threat to cellular integrity. It must be admitted that free radical perform some useful functions: the bactericidal action of leucocytes and in mediating inflammatory responses are notable examples, but it is when they are produced in large quantities and their metabolic products are allowed to go unchecked that they can seriously damage membranes and even denature DNA. Increased generation of free radicals in the biological systems over and above the potential of antioxidant mechanisms to curb them produces a state what is commonly known as oxidative (oxidant) stress in the body. Since free radicals are continuously being generated, the human body has developed a number of mechanisms to deal with their potentially damaging effects and those of their metabolites. The susceptibility of any tissue to an oxidative stress induced by free radicals or peroxide relates to the balance between the extent of that stress and the antioxidant ability of the protective agents present. 'Health' can be defined as an equilibrium state between the generation and scavenging of free radicals and peroxides. The cellular defense mechanisms and scavenging agents involve various enzymes such as superoxide dismutase, glutathione synthetase, glutathione peroxida6e, glutathione reductase, glucose-6-phosphate, dehydrogenase and catalase. Plasma proteins with antioxidant potential include the copper containing transferrin, ceruloplasmin and the iron containing transferrin. Foods constituents that also contribute to protection include the sulphur containing amino-acids and the minerals selenium, zinc and copper. In most pathological conditions the protective antioxidant mechanisms are overwhelmed leading to an elevated or rising state of free radicals and peroxides. Both Vitamin E and carotenoids can successfully deactivate super oxides (singlet oxygen) but when Vitamin E attacks the oxide it is destroyed. On the other hand beta-carotene can quench the oxide without damage to itself and thus can be used again and again and can convert singlet oxygen back to normal oxygen before it can cause damage leading to skin or lung cancer. Beta-carotene is also very efficient at trapping the free radicals.

Hence the present invention also encompasses that in the process of the preparation of formulations, there may be added adjuvants to the composition of the invention, such adjuvants being Vitamin C, Vitamin E, Compounds of selenium such as Selenium Dioxide and compounds of zinc such as Zinc Sulphate and additional amounts of commercially available natural-sourced carotenoids such as from fruits, vegetables and algae. The composition of typical preparations are described under respective examples.

The formulations of the invention are useful for the prophylactic or therapeutic treatment of subjects diagnosed to be carotenoid-deficient or Vitamin A-deficient or in need of protective efficacy of antioxidants known to be implicated in chronic disorders such as heart diseases, cancer, cataract and other chronic ailments. Both human and veterinary use is envisaged. The dosage per day is variable dependent on the age and weight of the subject to be treated and the severity of the condition as assessed by practicing medical physicians.

The following examples illustrate but do not limit the scope of the invention.

EXAMPLE 1

Fresh, hard, good quality reddish colored "Desi Red" carrots with a smooth surface, excluding those that were found defective, were selected and washed thoroughly with water. The sorted and washed carrots (1.0 kg) were subjected to crushing in a fruit mill to provide a comminution which was subjected to pressing through a filter press for the purpose of separating the pulp from the juice to provide a juice (ca. 600 ml). To the juice, 3 g of adipic acid was added with stirring. To the resulting mixture was added 60 g of sorbitol and the mixture was subjected to centrifuging to provide paste (ca. 17.2 g). The paste was dried under high vacuum. Pulverizing of the solid material and sieving gave the carotenoid powder of the invention (3.8 g). The composition of the product is given below.

Composition per 100 g Product from "Desi Red" Carrots (Example 1)

| | |
|---|---|
| beta-Carotene | 530 mg |
| alpha-Carotene | 27 mg |
| Lycopene | 700 mg |
| Lutein/Xeaxanthin | 15 mg |
| Total Carotenoids | 3750 mg |
| Proteins | 32.8 g |
| Carbohydrates | 4 g |
| Phosphorus | 647 mg |
| Lipids | 15.3 g |
| Vitamin C | 22 mg |
| Vitamin B1 | 5 mg |
| Vitamin B2 | 1 mg |
| Iron | 95 mg |
| Zinc | 1 mg |
| Manganese | 1 mg |
| Magnesium | 162 mg |
| Calcium | 1.381 g |
| Potassium | 1.99 g |
| Sodium | 1.99 g |
| Total Minerals (Ash value) | 6.87 g |

EXAMPLE 2

The "Bangalore local" carrots were processed according to the procedure described in Example 1. The composition of the product is given below.

Composition per 100 g Product from "Bangalore local" Carrots

| | |
|---|---|
| beta-Carotene | 2095 mg |
| alpha-Carotene | 31 mg |
| Lycopene | 70 mg |
| Lutein/Xeaxanthin | 13 mg |
| Total Carotenoids | 2948 mg |
| Phosphorus | 680 mg |
| Proteins | 31.5 g |
| Carbohydrates | 4.5 g |
| Lipids | 30.3 g |
| Vitamin C | 24 mg |
| Vitamin B1 | 6 mg |
| Vitamin B2 | 2 mg |
| Iron | 12 mg |
| Zinc | 1.4 mg |
| Manganese | 1 mg |
| Magnesium | 602 mg |
| Calcium | 894 mg |
| Potassium | 2 g |
| Sodium | 1 g |
| Total Minerals (Ash value) | 7.1 g |

EXAMPLE 3

The different supplies carrots were processed according to the procedures described in Examples 1 to 13. The composition of the powder was analyzed and shown to have values in the range as described below.

Range of composition per 100 g products from carrots (Daucus carota L)

| | | |
|---|---|---|
| beta-Carotene | 100–4000 | mg |
| alpha-Carotene | 10–300 | mg |
| Lycopene | 10–2000 | mg |
| Lutein/Xeaxanthin | 5–50 | mg |
| Total Carotenoids | 250–5000 | mg |

-continued

| | | |
|---|---|---|
| Proteins | 10–50 | g |
| Carbohydrates | 1–25 | |
| Phosphorus | 0.1–1 | g |
| Lipids | 20–40 | g |
| Vitamin C | 10–500 | mg |
| Vitamin B1 | 1–6 | mg |
| Vitamin B2 | 0.5–4 | mg |
| Iron | 5–100 | mg |
| Zinc | 1–5 | mg |
| Manganese | 0.1–1 | mg |
| Magnesium | 50–900 | mg |
| Calcium | 0.5–3 | g |
| Potassium | 1–4 | g |
| Sodium | 1–3 | g |
| Total Minerals (Ash value) | 3–10 | g |

EXAMPLE 4

The procedure described in Example 1 was followed using citric acid in place of adipic acid.

EXAMPLE 5

The procedure described in Example 1 was followed using fumaric acid in place of adipic acid.

EXAMPLE 6

The procedure described in Example 1 was followed using malic acid in place of adipic acid.

EXAMPLE 7

The procedure described in Example 1 was followed using tartaric acid in place of adipic acid.

EXAMPLE 8

The procedure described in Example 1 was followed using ascorbic acid in place of adipic acid.

EXAMPLE 9

The procedure described in Example 1 was followed using sorbic acid in place of adipic acid.

EXAMPLE 10

The procedure described in Example 1 was followed using mannitol in place of sorbitol.

EXAMPLE 11

The procedure described in Example 1 was followed using sucrose in place of sorbitol.

EXAMPLE 12

The procedure described in Example 1 was followed using lactose in place of sorbitol.

EXAMPLE 13

The procedure described in Example 1 was followed using dextrose in place of sorbitol.

EXAMPLE 14

Preparation of nutrient-rich carotenoids tablets.

Typical composition of Ingredients:

| | |
|---|---|
| Nutrient-rich carotenoid powder (cf Example 1) | 400 mg |
| Gelatin | 12 mg |
| Sucrose | 25 mg |
| Microcrystalline Cellulose | 25 mg |
| Starch | 60 mg |
| Talc | 5 mg |
| Magnesium stearate | 3 mg |
| Colloidal Silicon dioxide | 10 mg |
| Hydroxy Prophyl Methyl Cellulose | 15 mg |
| Titanium Dioxide | 0.5 mg |
| Sunset Yellow FCF | 4 mg |
| Propylene Glycol | 1 mg |

The tablets were prepared by blending nutrient-rich carotenoid powder with sucrose and Microcrystalline cellulose, granulating with Starch Gelatin paste, drying, lubricating with Talc, Magnesium stearate and Colloidal silicon dioxide followed by compression into tablets. For coating, Hydroxypropyl Methyl Cellulose, Propylene glycol and a blend of Titanium dioxide/Sunset Yellow FCF were used.

EXAMPLE 15

Preparation of nutrient-rich carotenoid in combination with other antioxidants in tablet form.
Typical composition of ingredients:

| | |
|---|---|
| Nutrient-rich carotenoid powder (cf Example 1) | 100 mg |
| Natural beta-carotene and carotenoids 20% | 15 mg |
| Vitamin E Acetate | 25 mg |
| Vitamin C | 150 mg |
| Selenium dioxide | 75 mcg |
| Zinc, sulphate | 70 mg |
| Microcrystalline Cellulose | 25 mg |
| Starch | 25 mg |
| Gelatine | 5 mg |
| Talc | 6 mg |
| Magnesium Stearate | 4 mg |
| Colloidal Silicon Dioxide | 6 mg |
| Hydroxypropyl Methyl Cellulose | 15 mg |
| Titanium Dioxide and Sunset Yellow FCF | 0.5 mg |
| Propylene Glycol | 1 mg |

Tablets were prepared by blending nutrient-rich carotenoid powder with Vitamin E acetate, Vitamin C, Selenium Dioxide and Zinc Sulphate. The blend was mixed with Microcrystalline Cellulose, granulated with Starch paste, dried, lubricated with Talc, Magnesium stearate and Colloidal Silicon Dioxide followed by compression into tablets. For coating, Hydropropyl Methyl Cellulose, Propylene glycol Titanium Dioxide and Sunset yellow FCF were used.

EXAMPLE 16

Preparation of tablets of nutrient-rich carotenoid with spirulina: typical composition of ingredients

| | |
|---|---|
| Nutrient-rich carotenoid Powder (ef example 1) | 250 mg |
| Spirulina | 250 mg |
| Microcrystalline Cellulose | 50 mg |
| Starch | 15 mg |
| Talc | 6 mg |
| Magnesium Stearate | 4 mg |
| Colloidal Silicon Dioxide | 6 mg |

The tablets were prepared by blending nutrient-rich carotenoid powder, Spirulina and Microcrystalline Cellulose, granulated with starch paste, dried, lubricated with Talc, Magnesium Stearate and Colloidal Silicon Dioxide and compressed into tablets.

EXAMPLE 17

Preparation of nutrient-rich carotenoid capsules
Typical composition of ingredients

| | |
|---|---|
| Nutrient-rich carotenoid powder (cf example 1) | 250 mg |
| Microcrystalline Cellulose | 100 mg |
| Talc | 7 mg |
| Magnesium Stearate | 2 mg |
| Colloidal Silicon Dioxide | 4 mg |

Nutrient-rich carotenoid powder was blended with Microcrystalline Cellulose, lubricated with Talc, Magnesium Stearate, Colloidal silicon dioxide and filled in the capsules.

EXAMPLE 18

Preparation of nutrient-rich carotenoid Soft Gelatin Capsules
Typical composition of ingredients

| | |
|---|---|
| Nutrient-rich carotenoid powder (cf example 1) | 250 mg |
| Vegetable oil | 250 mg |
| Soft gelatin capsule shell | one |

EXAMPLE 19

Preparation of nutrient-rich carotenoid powder mix
Typical composition of ingredients

| | |
|---|---|
| Nutrient-rich carotenoid powder (cf example 1) | 500 mg |
| Sucrose | 500 mg |

Nutrient-rich carotenoid powder was blended with sucrose and filled in 40 micron Aluminium-poly sachets.

EXAMPLE 20

Preparation of suspension of micronutrient-rich carotenoid paste
Typical composition of ingredients

| | |
|---|---|
| Nutrient-rich carotenoid paste (cf Example 1) | 20 g |
| Sucrose | 60 g |
| Purified water to make | 100 ml |

Nutrient-rich carotenoid paste was suspended in syrup prepared from sucrose and water.

EXAMPLE 21

Preparation of cream containing nutrient-rich carotenoid paste
Typical composition of ingredients

| | |
|---|---|
| Nutrient-rich carotenoid paste (cf Example 1) | 1 g |
| Vitamin E Acetate | 1 g |

| -continued | |
|---|---|
| Vitamin C | 1 g |
| Light Liquid Paraffin | 10 g |
| Propylene Glycol | 8 g |
| Cetostearyl alcohol | 7 g |
| Cetomacrogol - 1000 | 3.5 g |
| White Bees Wax | 2.5 g |
| Purified Water | 66 g |

A blend of nutrient-rich carotenoid paste, Vitamin E acetate and Vitamin C was incorporated in cream prepared from solution of Cetostearyl alcohol, Cetomacrogol 1000 and White beeswax in light liquid paraffin and water-propylene glycol mixture.

Tablets(Example 14) containing 400 mg of the composition equivalent to 1.2 mg of carotenoid were used for trials:

GROUP I 5 participants complaining of watering of eyes, redness and inability to open the eyes completely in sunlight were administered the tablets over a period of two weeks. Significant reduction of the symptoms were observed.

GROUP II 5 participants sensitive to continuous exposure to sunlight and suffering from skin erythema on longer exposure were administered the tablets over a period of four weeks. Significant reduction of the symptoms induced by long exposure were observed.

We claim:

1. A method of inducing antioxidant activity in warm-blooded animals comprising administering to warm-blooded animals an antioxidatingly effective amount of a biologically active composition comprising 0.25 to 5% by weight of an active carotenoid fraction extracted from carrots with a carboxylic acid at a pH of 3 to 6 followed by treatment with at least one saccharide based on the total weight of the composition and micro and macro nutrients sufficient to aid in the absorption acid assimilation of the carotenoid fraction and to supplement the action thereof.

2. The method of claim 1 wherein the composition also contains therapeutic amounts of at least one member of the group consisting of spirulina, Vitamin E, selenium compounds, zinc compounds, Vitamin C and carotenoids extracted from other natural sources.

3. The method of claim 1 wherein the macro nutrients include 20 to 40% by weight of the composition of lipids.

4. The method of claim 1 wherein the macro nutrients include 10 to 50% by weight of the total composition of proteins.

5. The method of claim 1 wherein the macro nutrients include 1 to 25% by weight of the total composition of carbohydrates.

6. The method of claim 1 wherein the micro nutrients include 0.01 to 1% by weight of the total composition of at least one vitamin selected from the group consisting of Vitamins $B_1$ and $B_1$, Niacin and Vitamin C.

7. The method of claim 1 wherein the micro nutrients include 3 to 10% by weight of the total composition of materials and trace elements.

8. The method of claim 1 wherein the carotenoid fraction includes α-carotene, β-carotene, Lutein, zeaxanthin and lycopene.

* * * * *